United States Patent
Han et al.

(10) Patent No.: US 10,744,065 B2
(45) Date of Patent: Aug. 18, 2020

(54) METHOD FOR CONTROLLING ACUPRESSURE FORCE AND BODY SCAN IN REAL-TIME

(71) Applicant: CERAGEM CO., LTD, Cheonan-si, Chungcheongnam-do (KR)

(72) Inventors: Sang Cheol Han, Asan-si Chungcheongnam-do (KR); Chang Su Park, Seongnam-si (KR); Hui Won Choi, Cheonan-si (KR); Han Rim Song, Paju-si (KR); Keun Young Paek, Cheonan-si (KR)

(73) Assignee: CERAGEM CO., LTD, Cheonan-si, ChungCheongNam-do (KR)

( * ) Notice: Subject to any disclaimer, the term of this patent is extended or adjusted under 35 U.S.C. 154(b) by 173 days.

(21) Appl. No.: 15/763,114

(22) PCT Filed: Sep. 21, 2016

(86) PCT No.: PCT/KR2016/010503
§ 371 (c)(1),
(2) Date: Mar. 25, 2018

(87) PCT Pub. No.: WO2017/052173
PCT Pub. Date: Mar. 30, 2017

(65) Prior Publication Data
US 2019/0053979 A1    Feb. 21, 2019

(51) Int. Cl.
*A61H 39/04*      (2006.01)
*A61H 39/06*      (2006.01)
(Continued)

(52) U.S. Cl.
CPC ........... *A61H 39/04* (2013.01); *A61B 5/1072* (2013.01); *A61B 5/684* (2013.01); *A61B 5/6843* (2013.01);
(Continued)

(58) Field of Classification Search
CPC ........ A61H 9/00; A61H 9/007; A61H 9/0021; A61H 2201/0196; A61H 39/04;
(Continued)

(56) References Cited

U.S. PATENT DOCUMENTS 5,545,177 A    8/1996  Coseo
5,792,080 A *  8/1998  Ookawa ................... A61H 1/00
                                                    601/102

(Continued)

FOREIGN PATENT DOCUMENTS

CA          1310373 C       11/1992
CL          1582-1993       12/1993
(Continued)

*Primary Examiner* — Kathleen S Holwerda
*Assistant Examiner* — Kankindi Rwego
(74) *Attorney, Agent, or Firm* — Don D. Cha; HDC IP Law, LLP

(57) ABSTRACT

The present invention relates to a method for controlling an acupressure force and a body scan in real-time and, more specifically, the method comprises the steps of: (a) setting a reference vertical height for each horizontal position of an acupressure part, and setting a target acupressure force within the range of the reference vertical height; (b) calculating a current measurement acupressure force by means of a user's load measurement data applied to a load cell; and (c) comparing the target acupressure force with the current measurement acupressure force so as to control the vertical height of the acupressure part. That is, the present invention presents a method for controlling a body scan in real-time, the method enabling: an inflection point of a driving current measurement value applied to a horizontal driving motor to be measured during the horizontal driving of an acupressure part in an initial massage process, so as to reflect, on an acupressure force correction value, a deviation between a vertical position of the acupressure part corresponding to the inflection point and a reference vertical position, for each (Continued)

horizontal position, stored in a database, thereby calculating a new target acupressure force; and the new target acupressure force to be reflected in acupressure control such that an acupressure force suitable for a user can be provided during a massage.

8 Claims, 13 Drawing Sheets

(51) Int. Cl.
*A61H 15/02* (2006.01)
*A61H 39/02* (2006.01)
*A61B 5/00* (2006.01)
*A61B 5/107* (2006.01)
*G16H 20/30* (2018.01)
*A61H 15/00* (2006.01)

(52) U.S. Cl.
CPC ............ *A61H 15/02* (2013.01); *A61H 39/02* (2013.01); *A61H 39/06* (2013.01); *G16H 20/30* (2018.01); *A61H 2015/0014* (2013.01); *A61H 2201/0196* (2013.01); *A61H 2201/0207* (2013.01); *A61H 2201/1223* (2013.01); *A61H 2201/1626* (2013.01); *A61H 2201/1673* (2013.01); *A61H 2201/5002* (2013.01); *A61H 2201/5007* (2013.01); *A61H 2201/5028* (2013.01); *A61H 2201/5061* (2013.01); *A61H 2201/5071* (2013.01); *A61H 2205/081* (2013.01)

(58) Field of Classification Search
CPC .... A61H 2009/0014; A61H 2015/0007; A61H 2015/0014; A61H 2015/0021; A61H 2015/0028; A61H 2015/0035; A61H 2015/0042; A61H 2015/005; A61H 2015/0064; A61H 2015/0071; A61H 2015/0078; A61H 15/00; A61H 15/02; A61H 39/00; A61H 39/02; A61H 39/06; A61H 2201/0207; A61H 2201/1223; A61H 2201/1626; A61H 2201/1673; A61H 2201/5002; A61H 2201/5007; A61H 2201/5028; A61H 2201/5061; A61H 2201/5071; A61H 2205/081; G16H 20/30; A61B 5/1072; A61B 5/684

USPC ........................................................ 606/204
See application file for complete search history.

(56) References Cited

U.S. PATENT DOCUMENTS

2013/0110007 A1 5/2013 Jeon et al.
2014/0277300 A1 9/2014 Lee et al.

FOREIGN PATENT DOCUMENTS

| CL | 201800775 | | 7/2019 |
| CN | 2933388 | Y | 8/2006 |
| CN | 102727209 | | 7/2011 |
| CN | 202761678 | U | 3/2013 |
| CN | 204246132 | U | 4/2015 |
| EP | 06125951 | | 5/1994 |
| EP | 1145700 | A1 | 10/2001 |
| EP | 2638889 | A2 | 9/2013 |
| EP | 16848899.7 | | 7/2019 |
| JP | H06-125951 | A | 5/1994 |
| JP | 2007014442 | A | 1/2007 |
| JP | 2009-050578 | A | 3/2009 |
| JP | 2009142543 | A | 7/2009 |
| JP | 4982199 | B2 | 7/2012 |
| JP | 2018-515283 | | 2/2019 |
| KR | 20040000263 | A | 1/2004 |
| KR | 100467982 | B1 | 1/2005 |
| KR | 100495450 | B1 | 6/2005 |
| KR | 10-05443850000 | | 1/2006 |
| KR | 2020060011420 | | 7/2006 |
| KR | 10-0865259 | B1 | 10/2008 |
| KR | 100984026 | B1 | 9/2010 |
| KR | 10-1185100 | B1 | 9/2012 |
| KR | 10-11851000000 | | 9/2012 |
| KR | 101230665 | B1 | 2/2013 |
| KR | 101351169 | B1 | 1/2014 |
| KR | 103908391 | A | 3/2014 |
| KZ | 2018/0249.1 | | 9/2016 |
| RU | 2153316 | C2 | 7/2000 |
| RU | 2472432 | C1 | 1/2013 |
| RU | 2018114310/14 | | 9/2016 |
| SG | 11201802414 | W | 5/2019 |
| WO | WO 2011/105179 | A1 | 2/2011 |
| WO | 2015/121695 | A1 | 8/2015 |

* cited by examiner

METHOD FOR CONTROLLING ACUPRESSURE FORCE AND BODY SCAN IN REAL-TIME

CROSS-REFERENCE TO THE RELATED APPLICATIONS

The present application claims priority based on Korean Patent Application No. 10-2015-0136424 filed on Sep. 25, 2015, the disclosure of which is incorporated herein by reference in its entirety.

FIELD OF THE INVENTION

The present invention relates to a method of controlling acupressure power and a human body scan in real-time, in which in order to calculate a target acupressure power according to a user during a acupressure power control in real-time using an automatically-driven acupressure section, an inflection point of a current of a horizontal driving motor is measured during a horizontal driving of the acupressure section, and a target acupressure power is calculated by reflecting a deviation between a vertical position of the acupressure section at a corresponding position and a reference vertical position for each horizontal position stored in a database to an acupressure power correction value.

BACKGROUND OF THE INVENTION

In general, acupressure is a hand therapy that aims to promote health or treat diseases by applying a pressure to a predetermined part of the surface of a human body, and different effects are provided by increasing or decreasing acupressure power or keeping the acupressure power constant.

A general acupressure treatment is achieved by vertically applying a pressure to a predetermined part, keeping the pressure constant for a predetermined time, and then releasing the pressure. In order to keep the pressure constant, a process of measuring the current pressure and correcting the pressure is needed.

The conventional automatic heaters provide acupressure power using a pressing force applied to an acupressure section according to a weight of a user, and a magnitude of the acupressure power is proportional to a magnitude of the weight, and for the same weight, the magnitude of the acupressure power varies according to the distribution of loads applied to the product.

Here, the distribution of loads refers to difference in the degree to which the weight of the user is assigned in each position of the product. When the load due to the weight of the user is concentrated on a massager, the magnitude of the acupressure power increases, and when the load due to the weight of the user is concentrated on other structures, such as foam, the magnitude of the acupressure power decreases.

When the acupressure section is lifted, the load is concentrated on the massager in comparison to that of the previous state, so that the magnitude of the acupressure power is increased. In contrast, when the acupressure section is lowered, the load is concentrated on other structures excluding the massager, so that the magnitude of the acupressure power is decreased. By using this principle, the magnitude of the acupressure power is controlled.

The conventional automatic heaters adopt a concept of acupressure power control using a vertical height of the acupressure section. However, since there is no device to measure the current acupressure power, an increase or decrease in the acupressure power is only achievable based on the current acupressure power, so the conventional automatic heaters cannot implement the acupressure power at a specific value.

In addition, the conventional automatic heaters have an acupressure power control algorithm in which a horizontal position corresponding to a position of a spine bone of the user is measured through a process of a body scan, a vertical height corresponding to a massage strength at the corresponding position is calculated, and the acupressure section is controlled to be moved to a vertical position corresponding to the vertical height whenever the acupressure section passes through the corresponding horizontal position.

However, when the user moves during the massage and thus the position of the spine bone is changed, or the user is changed with another user, the vertical position also needs to be changed according to the changes. However, the massage process is controlled to use a previously stored vertical position, thus causing a difference between an actual acupressure power and an intended acupressure power.

This is because the massage process is performed with acupressure power corresponding to a previously-stored position of a spine bone, that is, a previously-stored vertical position of the acupressure section even when the position of the spine bone of the user is changed, and there is a limitation in obtaining an optimum effect of massage with a result in which a displacement value according to a spine bone displacement caused by the user is not reflected.

RELATED ART DOCUMENT

Korean Registered Patent No.: 10-0495450 (2005.06.04.)

Technical Problem

The present invention has been made to solve the above-described problems, and the present invention is directed to providing a technology for providing acupressure power appropriate for a user by measuring an inflection point of a measured value of a driving current applied to a horizontal driving motor during a horizontal driving of an acupressure section in an initial massage process, calculating a new target acupressure power by reflecting a deviation between a vertical position of the acupressure section corresponding to the inflection point and a reference vertical position for each horizontal position stored in a database to an acupressure power correction value, and reflecting the new target acupressure power to an acupressure power control.

The present invention is also directed to providing a technology in which when the position of a user is changed during a massage or the user is changed with another user and thus scan information is changed, a changed position of a spine is actively tracked using real-time human body scan information, and acupressure power is provided at an accurate position.

Technical Solution

One aspect of the present invention provides a method of controlling acupressure power in real-time, the method including the steps of: (a) setting a reference vertical height for each horizontal position of an acupressure section and setting a target acupressure power within a range of the reference vertical height; (b) calculating a current measured acupressure power from measured data of a load of the user applied to a load cell; and (c) comparing the target acupressure power with the current measured acupressure power and controlling a vertical height of the acupressure section by.

In step (c), the acupressure section may vertically descend or vertically ascend when the current measured acupressure power is higher than the target acupressure power or the current measured acupressure power is lower than the target acupressure power, and the acupressure section may stop vertical driving when the current measured acupressure power is equal to the target acupressure power.

When a current vertical height of the acupressure section is outside the range of the reference vertical height, the measured acupressure power may be assigned a predetermined margin value.

Step (a) may further include (a') adopting the target acupressure power with a minimum value and determining a specific horizontal position corresponding to an inflection point of a driving current-measured value applied to a horizontal driving motor during forward and backward movement of the acupressure section.

The method may further include calculating a correction value for the target acupressure power by using a deviation between a vertical height of the acupressure section at the specific horizontal position and the reference vertical height at the specific horizontal position.

The inflection point of the driving current-measured value may be calculated as a specific spine position of a current user, and when a current spine position corresponding to the driving current-measured value applied to the horizontal driving motor during a horizontal movement of the acupressure section in a massage process is different from the specific spine position, a position of an acupoint may be corrected with an offset by a deviation between the current spine position and the specific spine position.

When a distance ratio for acupoints of previous spine positions is changed to a distance ratio for acupoints of current spine positions due to a change of a user, a ratio for the acupoints may be corrected.

Another aspect of the present invention provides a method of controlling a human body scan in real-time, the method including the steps of: (A) collecting electric current variation-value data according to a driving of a horizontal motor, setting a variation section of a current, and extracting position information at acupoints corresponding to a maximum inflection point and a minimum inflection point of the variation section; (B) when a position of an acupoint of a current user during a massage process is different from the position of the acupoint corresponding to step (A), calculating a correction value according to a difference between the positions; and (C) correcting the positions of the respective acupoints of the current user by the correction value calculated in step (B).

When a distance between acupoints of the current user during the massage process is different from a distance between previous acupoints extracted in step (A), a distance ratio for the acupoints of the current user may be corrected by a ratio of the distance between the current acupoints and the distance between the previous acupoints.

Advantageous Effects

A method of controlling acupressure power and a human body scan in real-time according to the present invention can enable optimum control of a massage strength according to a body condition of a user by calculating a new target acupressure power according to the changed position of a spine bone with respect to the position of the current user when the user changes the position thereof or the user is changed with another user, and reflecting the calculated new target acupressure power to the acupressure power control.

A method of controlling acupressure power and a human body scan in real-time according to the present invention can provide a real-time user-customized massage by using an inflection point of a driving current-measured value of a horizontal driving motor for a horizontal driving of an acupressure section, detecting a specific tracking position corresponding to the inflection point during a massage process in real-time, and reflecting the detected specific tracking position in the control of the acupressure section, and can maximize the working efficiency by obviating the need for an additional human body scan process that is required in the conventional technology.

DETAILED DESCRIPTION OF THE INVENTION

Hereinafter, a method of controlling acupressure power and a human body scan in real-time according to the present invention will be described in detail with reference to the accompanying drawings.

Figure 1:
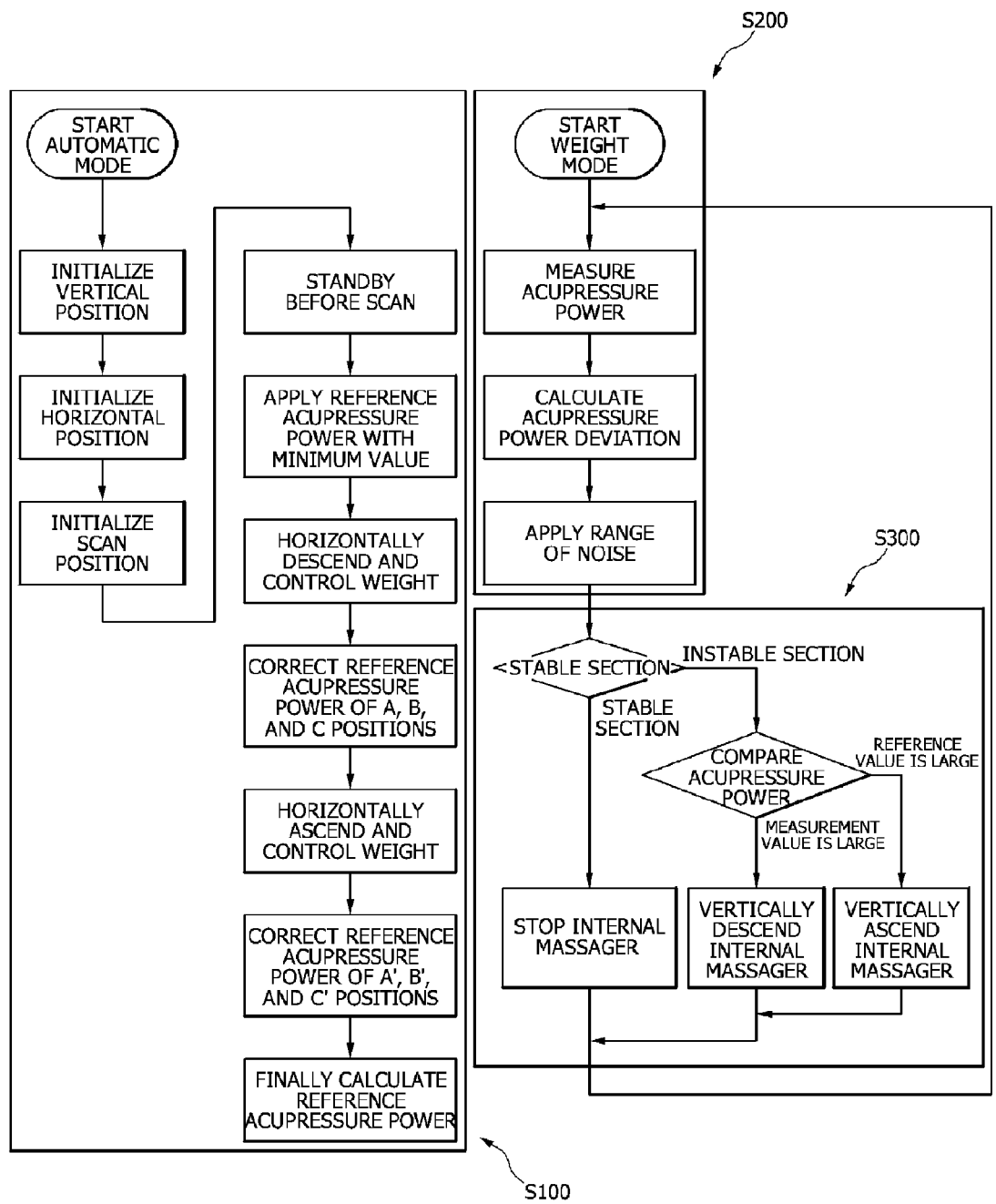
FIG. 1 is a flowchart showing a method of controlling acupressure power control in real-time according to the present invention.
Figure 3:
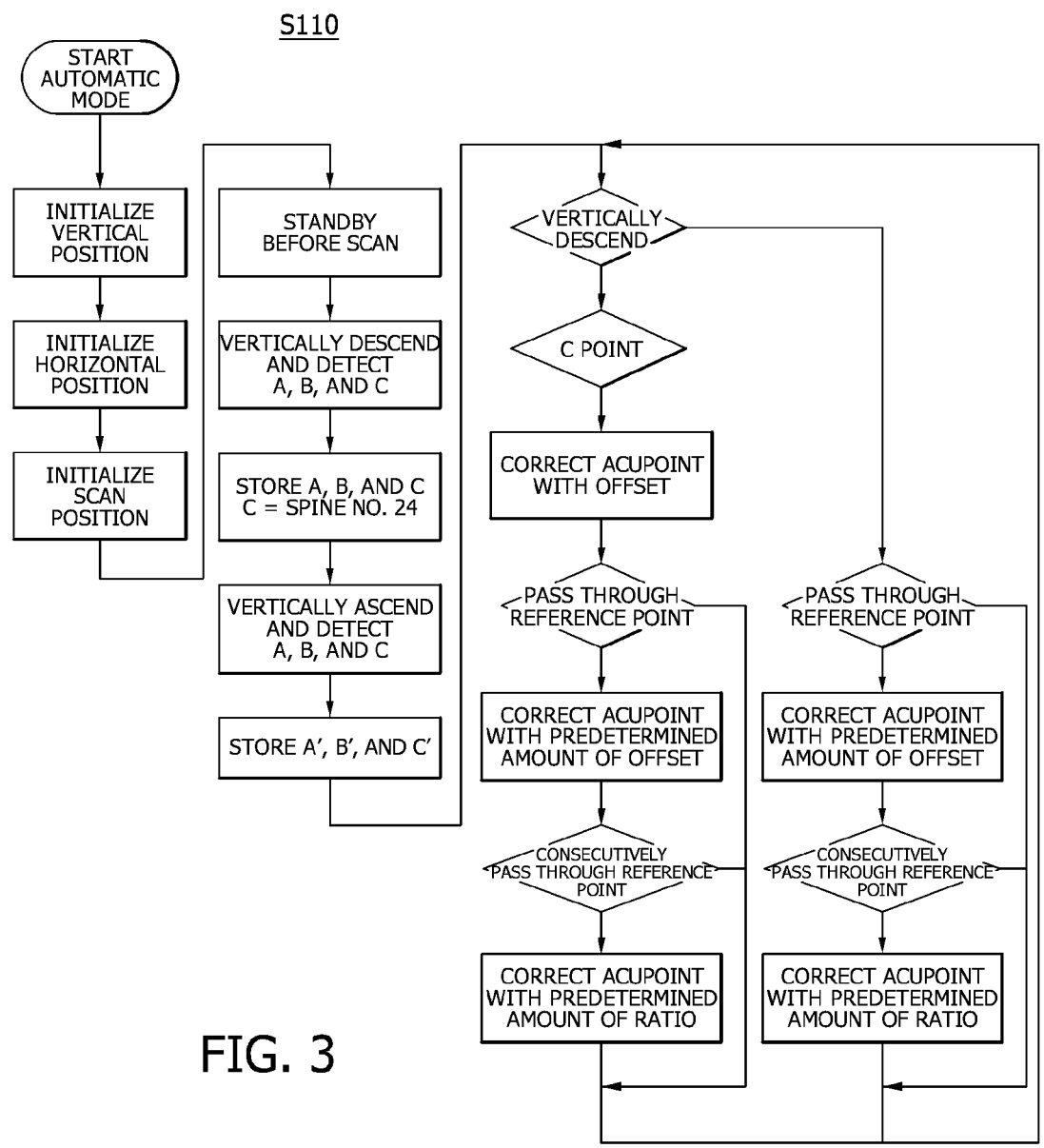
FIG. 3 is a flowchart showing a method of controlling a human body scan in real-time according to the present invention.

Referring to FIGS. 1 and 3, the method of controlling acupressure power and a body scan according to the present invention includes (a) setting a reference vertical height for each horizontal position of an acupressure section and setting a target acupressure power within a range of the reference vertical height (S100), (b) calculating a current measured acupressure power from measured data of a load of a user applied to a load cell (S200); and (c) comparing the target acupressure power with the current measured acupressure power and controlling a vertical height of the acupressure section (S300).

Figure 2:
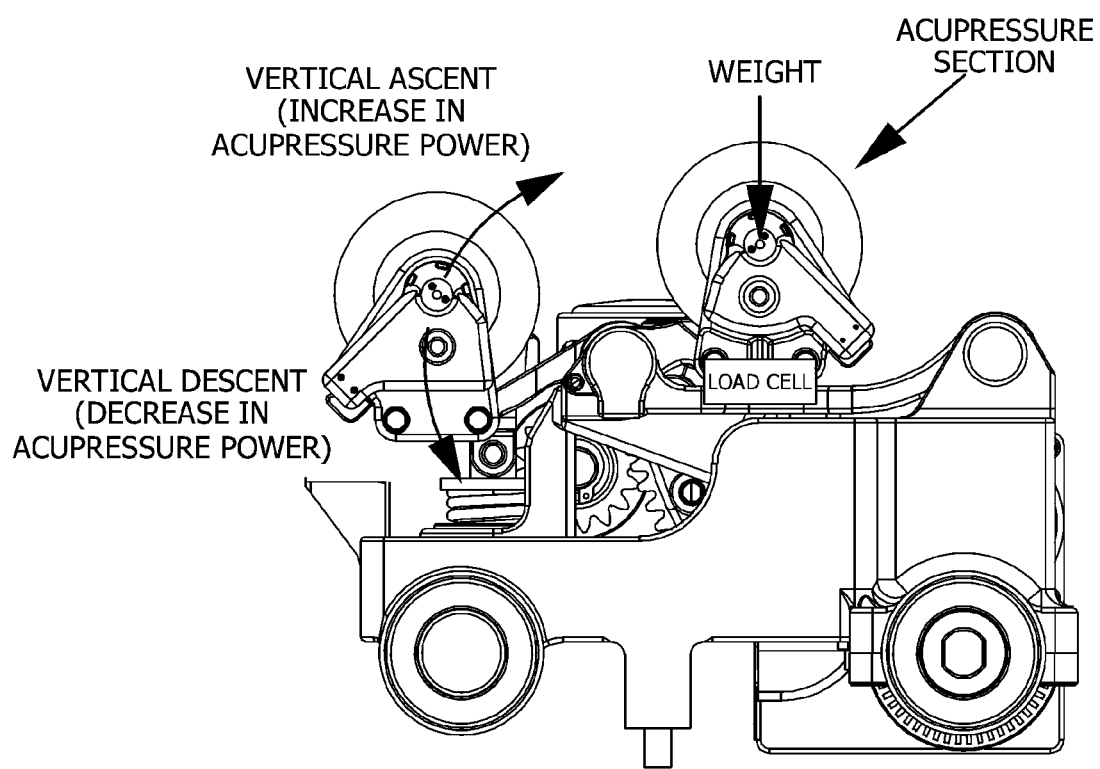
FIG. 2 is a side view illustrating a driving module employed in a method of controlling acupressure power and a human body scan in real-time.

Referring to FIGS. 1 to 3, step (a) in operation S100 according to the present invention is a process of setting a reference vertical height for each horizontal position of an acupressure section and setting the target acupressure power within the range of the reference vertical height.

First, a heater according to the present invention includes a driving module for driving an acupressure section, the driving module including a horizontal and vertical driving motor implemented as a brushless direct current (BLDC) motor and an acupressure section implemented as massage members arranged in two arrays in a front-to-back direction, and a load cell is disposed under the acupressure section to measure the load of the user.

As shown in FIGS. 1 to 3, step (b) in operation S200 according to the present invention is a process of calculating a measured acupressure power by measuring the load of the user using the load cell.

That is, the weight applied to an upper side of the acupressure section is transferred to the load cell through the acupressure section, and an electric signal of the load cell changed according to the applied weight is determined as a changed amount of weight through a control circuit.

In response to change in the measured amount of weight, the control circuit may control the magnitude of the acupressure power by lifting or lowering the acupressure section, so that a constant acupressure power is implemented.

One of the main characteristics of a method of controlling acupressure power of the heater according to the present invention is that the acupressure power control is implemented in real-time.

That is, the conventional method of controlling acupressure power of a heater is achieved in a way that horizontal positions corresponding to positions of spine bones of a user are detected through a process of a body scan, a vertical height corresponding to massage strength at the corresponding position is calculated, and the acupressure section is controlled to be moved to a vertical position corresponding to the vertical height whenever the acupressure section passes through the corresponding horizontal position.

Accordingly, when the position of the spine bone is moved according to movement of the user during a massage process, the vertical position needs to be changed according to the movement of the position of the spine bone, but the massage process is controlled based on a previously stored vertical position, thereby causing a difference between an actual acupressure power and an intended acupressure power.

However, the method of controlling a human body scan in real-time according to the present invention calculates a vertical position corresponding to a current horizontal position of the acupressure section in real-time through measurement and analysis of acupressure power, so that the acupressure power is accurately controlled to reach a target value regardless of movement of the user.

In this case, the target acupressure power may be set to be different or the same between horizontal positions, so that the acupressure power may be controlled to be different between sub-divisions or controlled to be the same over all divisions.

Referring to FIGS. 1 to 3, step (c) in operation S300 according to the present invention is a process of controlling the vertical height of the acupressure section by comparing the target acupressure power with a measured acupressure power.

To this end, the heater according to the present invention has a vertical position of the acupressure section fixed at a highest limit and a lowest limit as shown in FIG. 3, and while moving the acupressure section from a position of the spine Number 1 of the user to a maximum horizontal stroke section through a horizontal driving, collects weight-measured data through the load cell along the horizontal positions of the acupressure section.

Through the data, it can be seen that a difference exists in the acupressure power that varies with the control of the vertical height of the acupressure section according to the horizontal position.

Figure 4:
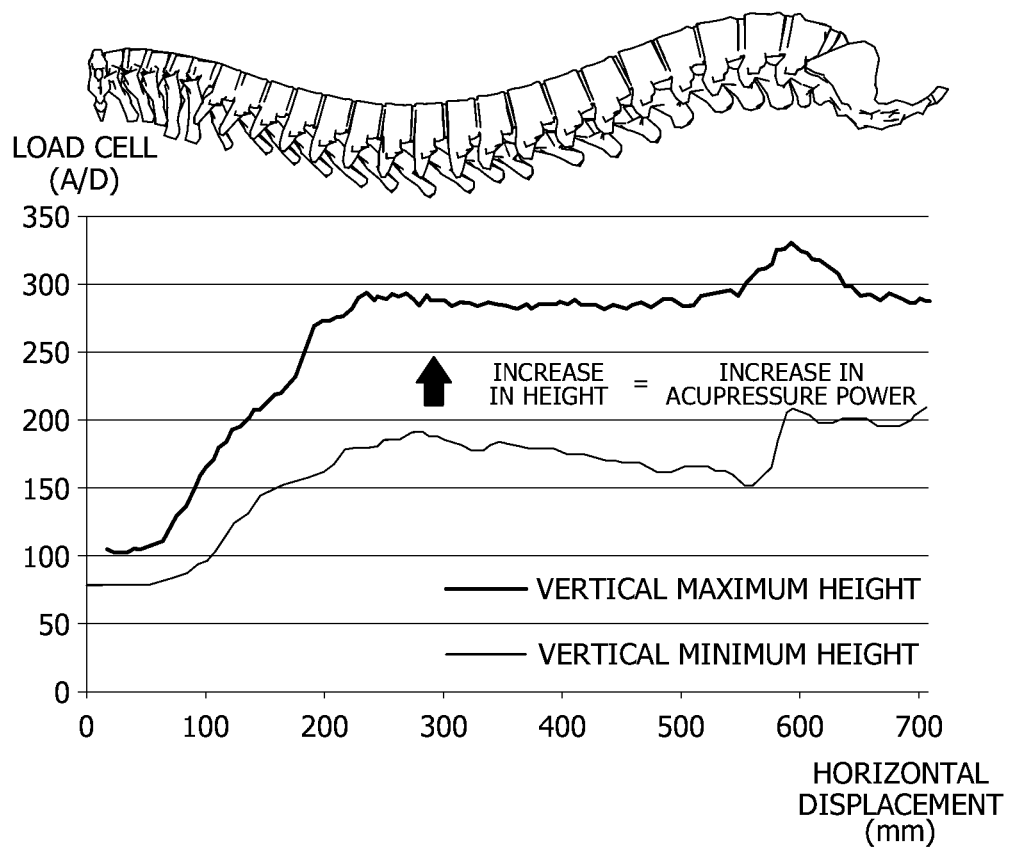
FIG. 4 is a graph showing a weight-measured data of a load cell with the change of a vertical height and a horizontal displacement of an acupressure section according to the present invention.

For example, in FIG. 4, it can be seen that the lowest limit of the vertical height is about 180 A/D and the highest limit of the vertical height is about 290 A/D from the load cell data at a position of horizontal displacement of 300 mm, and thus the acupressure power may be implemented in the range of 180 A/D to 290 A/D through the control of the vertical height of the acupressure section at the position of horizontal displacement of 300 mm.

The acupressure power control operation starts by setting the target acupressure power to 240 A/D with the lowest limit of the vertical height at the position of horizontal displacement of 300 mm, the acupressure power control operation stops when the measured acupressure power reaches 240 A/D, identical to the target acupressure power, while the vertical height of the acupressure section is being increased, so that the target acupressure power of 240 A/D is achieved.

This can be expressed as the following conditional expression.

If (target acupressure power>measured acupressure power) then perform vertical ascent drive;

Else if (target acupressure power<measured acupressure power) then perform vertical descent drive;

Else stop vertical drive.

Figure 5:
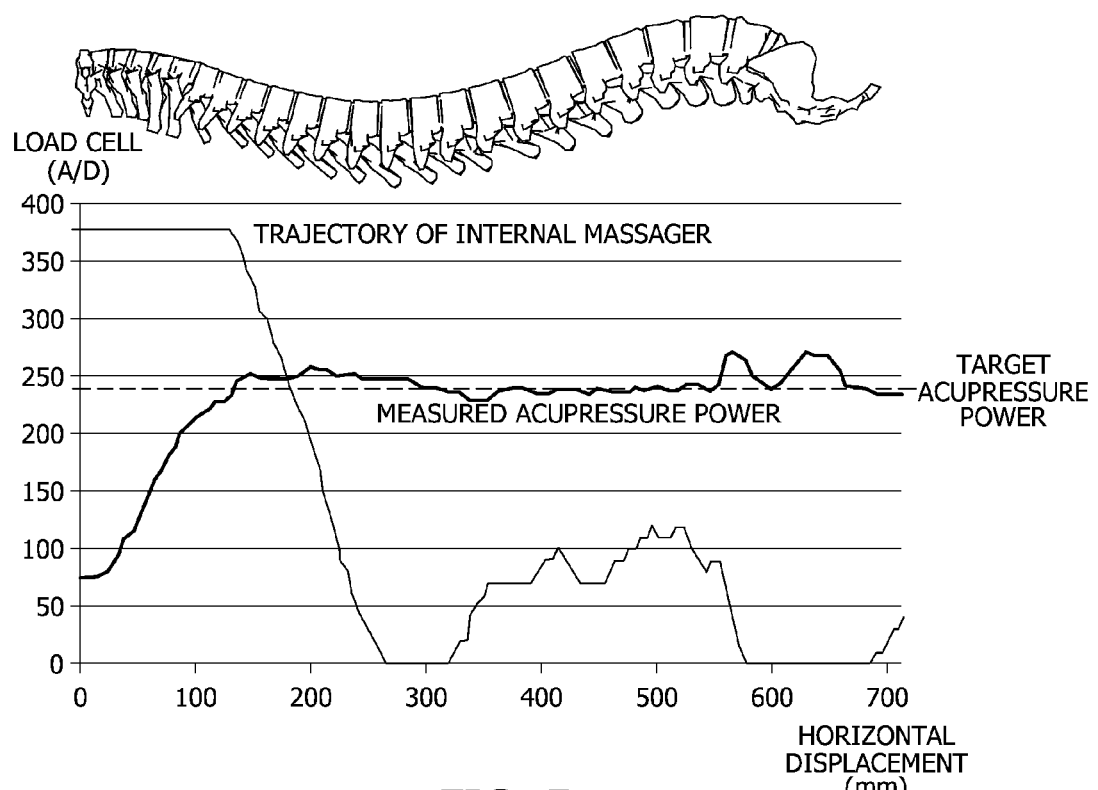
FIG. 5 is a graph showing a result of applying the method of controlling acupressure power in real-time according to the present invention at a specific target acupressure power.

In addition, FIG. 5 is a result of applying the method of controlling acupressure power in real-time, in which when the target acupressure power is set to 240 A/D and then the heater moves from the position of the spine Number 1 to the maximum horizontal-stroke section of the heater through a horizontal driving, a measured acupressure power is provided as 240 A/D, which is the target acupressure power, within the range of vertical movability of the acupressure section in the same manner as described above.

According to the above-described result, when the measured acupressure power is lower than 240 A/D, the acupressure section is vertically driven upward, and in contrast, when the measured acupressure power is higher than 240 A/D, the acupressure section is vertically driven downward, and when the measured acupressure power is 240 A/D, the acupressure section is not driven and stays in a vertical stop state, so that the target acupressure power of 240 A/D is achieved over the all massage divisions.

However, the control is performed within the range of vertical driving, and when the acupressure section is positioned at the vertically lowest limit, the acupressure power may not be decreased any more, and when the acupressure section is positioned at the vertically highest limit, the acupressure power may not be increased any more.

In this case, when an actual control environment is configured, the load cell measurement value may have a fluctuation due to noise and thus the measured acupressure power may also have a fluctuation.

Accordingly, there is a need to apply a range of noise to the target acupressure power, and a value two times the noise of the currently implemented circuit is determined to be suitable as the range.

The above-described conditional expression may be changed as follows when the range of noise is applied.

If (target acupressure power>(measured acupressure power+range of noise)) then perform vertical ascent drive;

Else if (target acupressure power<(measured acupressure power−range of noise)) then perform vertical descent drive;

Else stop vertical drive.

In the case in which the range of noise is set to 10 A/D in the result shown in FIG. 5, when the measured acupressure power is higher than 250 A/D with respect to the target acupressure power of 240 A/D, the acupressure section is vertically driven downward, and in contrast, when the measured acupressure power is lower than 230 A/D, the acupressure section is vertically driven upward.

When the measured acupressure power falls in a range of 230 A/D to 250 A/D, the acupressure section is in a vertical drive stop state, which is considered an acupressure power control stabilized state, and when the acupressure section is vertically driven as described above, the acupressure section is considered an acupressure power control instabilized state, for the sake of convenience of description.

The method of controlling acupressure power in real-time may be implemented using the example described above. However, when the user is changed, a different target acupressure power needs to be applied according to a current use.

Figure 6:
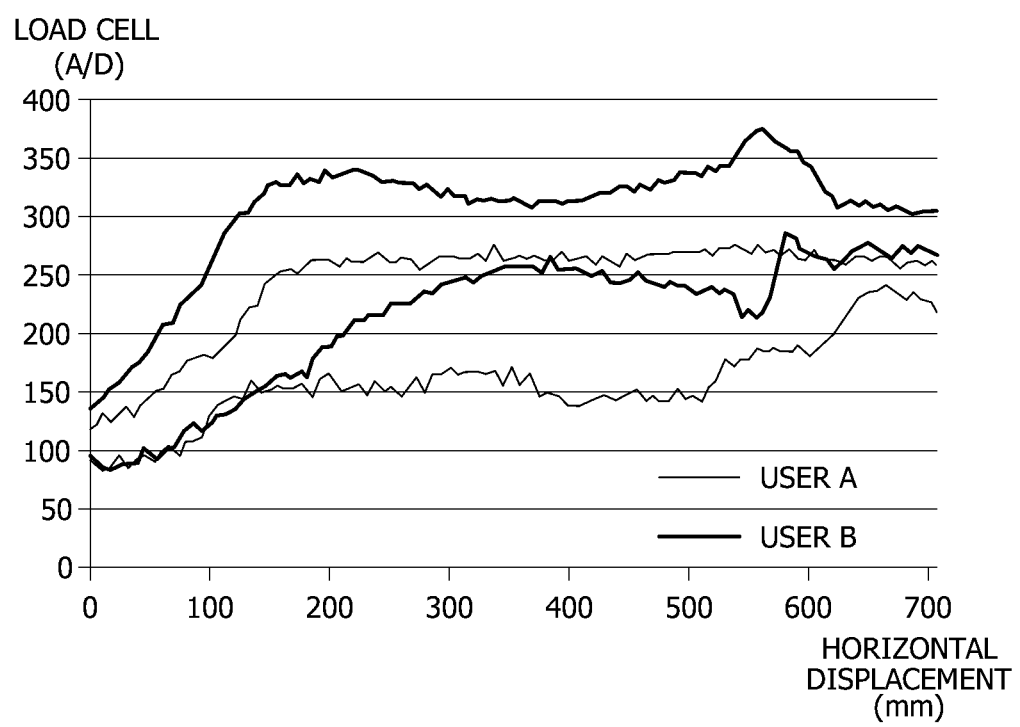
FIG. 6 is a graph showing different ranges of measured acupressure power according to users' body types.

FIG. 6 shows different ranges of measured acupressure power according to body types of users, which are measured during movement from the position of the spine Number 1 of the user to the maximum horizontal stroke section of the heater through horizontal driving with the vertical position of the acupressure section fixed at the highest limit and the lowest limit.

That is, in the case of user A (light weight), the load cell data changes in a range of 170 A/D to 260 A/D at the horizontal displacement point of 300 mm, and in the case of user B (heavy weight), the load cell data changes in a range of 250 A/D to 320 A/D at the horizontal displacement point of 300 mm.

When a proper target acupressure power is assumed as a middle level of the range, the middle level of 215 A/D for user A and the middle level of 285 A/D for user B do not match each other, and when the target acupressure power of 285 A/D for user B is applied to user A, the target acupressure power of 285 A/D exceeds the maximum acupressure power that is implementable through the vertical driving of the acupressure section, and thus is not considered the proper target acupressure power.

As such, the target acupressure power is different for each user, and an application of an improper target acupressure power leads to a deviation from the range implemented through a vertical driving of the acupressure section, so that the method of controlling acupressure power in real-time cannot be employed.

Accordingly, a control method of automatically calculating a different target acupressure power for each user needs to be considered.

That is, the control method of automatically calculating a different target operates based on a principle correcting the target acupressure power using a vertical height of the acupressure section at a specific horizontal position.

Figure 7:
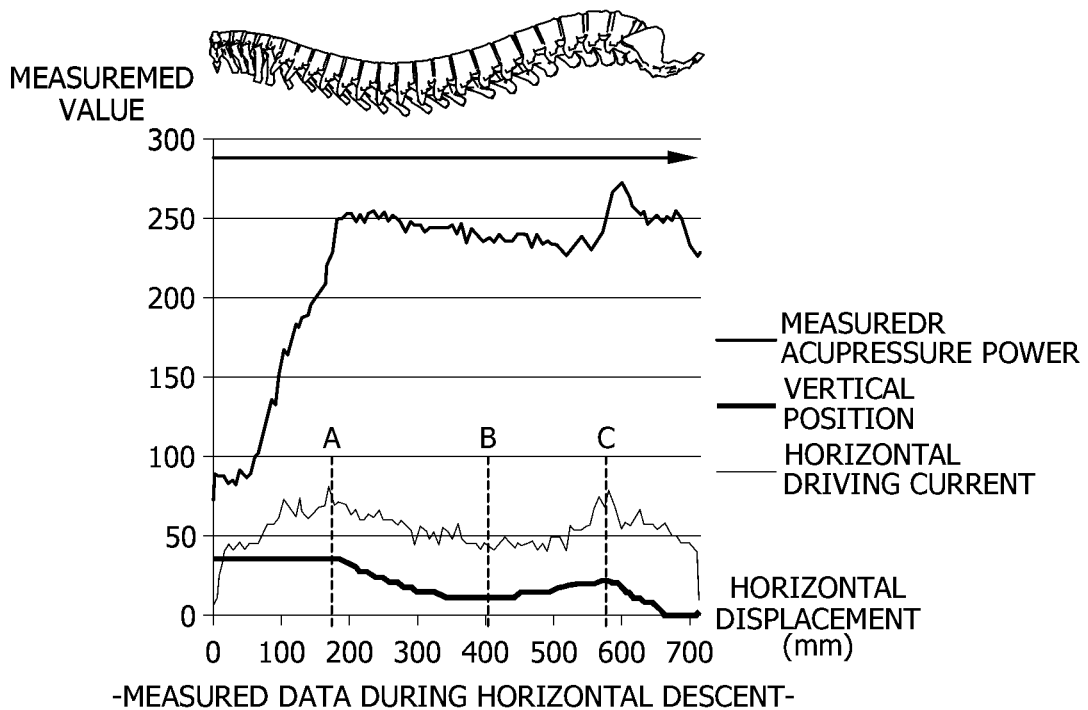
FIG. 7 is a graph showing a measured data during a reference horizontal descent and ascent at the specific target acupressure power according to the present invention.
Figure 7:
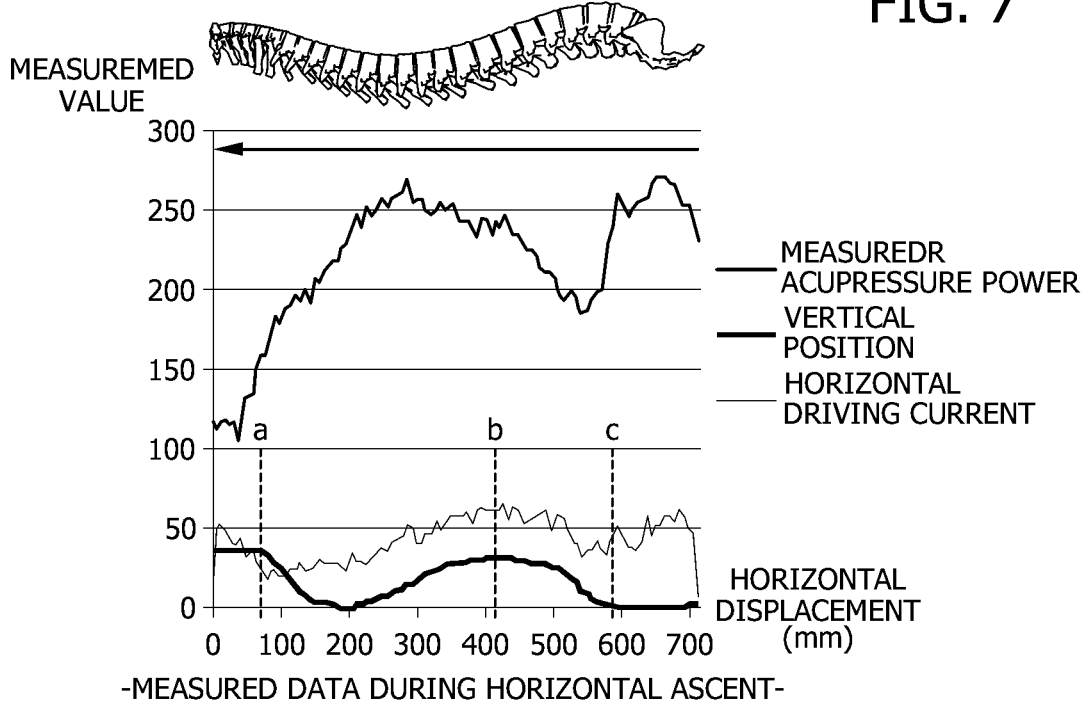

That is, FIG. 7 is a result of applying the method of controlling acupressure power in real-time based on the target acupressure power of 240 A/D to a specific user, whereby a specific horizontal position may be distinguished during a forward movement (hereinafter, referred to a 'horizontal descent') and a backward movement (hereinafter, referred to a 'horizontal ascent'), and a target acupressure power correction value may be calculated using a vertical height of the acupressure section at the distinguished specific horizontal position.

In this case, the specific horizontal position is distinguished or determined using an inflection point of a driving current-measured value of the horizontal driving motor that is adopted for a horizontal movement of the acupressure section.

The horizontal driving current represents three inflection points for each of the horizontal descent and the horizontal ascent with respect to the entire massage section regardless of the target acupressure power, and a horizontal position of the acupressure section is referred to as a specific horizontal position.

Hereinafter, the method of controlling a human body scan in real-time according to an inflection point distinguishment method using a horizontal driving current will be described in detail.

First, referring to FIG. 3, the method of controlling a human body scan in real-time according to the present invention includes the steps of (A) setting a variation section of current by collecting data of electric current variation value according to a driving of the horizontal motor and extracting position information at acupoints corresponding to a maximum inflection point and a minimum inflection point of the variation section; (B) when a position of an acupoint of a current user during a massage process is different from a position of the acupoint corresponding to step (A), calculating a correction value according to a difference between the positions; and (C) correcting the positions of the respective acupoints of the current user by the correction value calculated in step (B).

In this case, the method of controlling a human body scan in real-time according to the present invention is included in (a') determining a specific horizontal position corresponding to the inflection point of a measured value of a driving current applied to the horizontal driving motor during a horizontal descent or ascent of the acupressure section (S110) in the above-described method of controlling acupressure power in real-time.

Step (A) according to the present invention is a method of detecting positions of acupoints that are different for each user, in which a specific position of a spine of the user is tracked by using a change in a repulsive force applied to the acupressure section during a horizontal movement of the acupressure section with respect to the entire spine section of the user, and which is implemented using a driving current of the horizontal driving motor.

Since the position of an acupoint is associated with a specific position of the spine, the tracking of a specific position of the spine represents tracking the position of an acupoint.

Accordingly, driving current data of the horizontal driving motor is collected as shown in FIG. 7 when the acupressure section is moved from the position of the spine Number 1 to the maximum horizontal stoke section of the heater through a horizontal driving with the vertical position thereof fixed.

Figure 8:
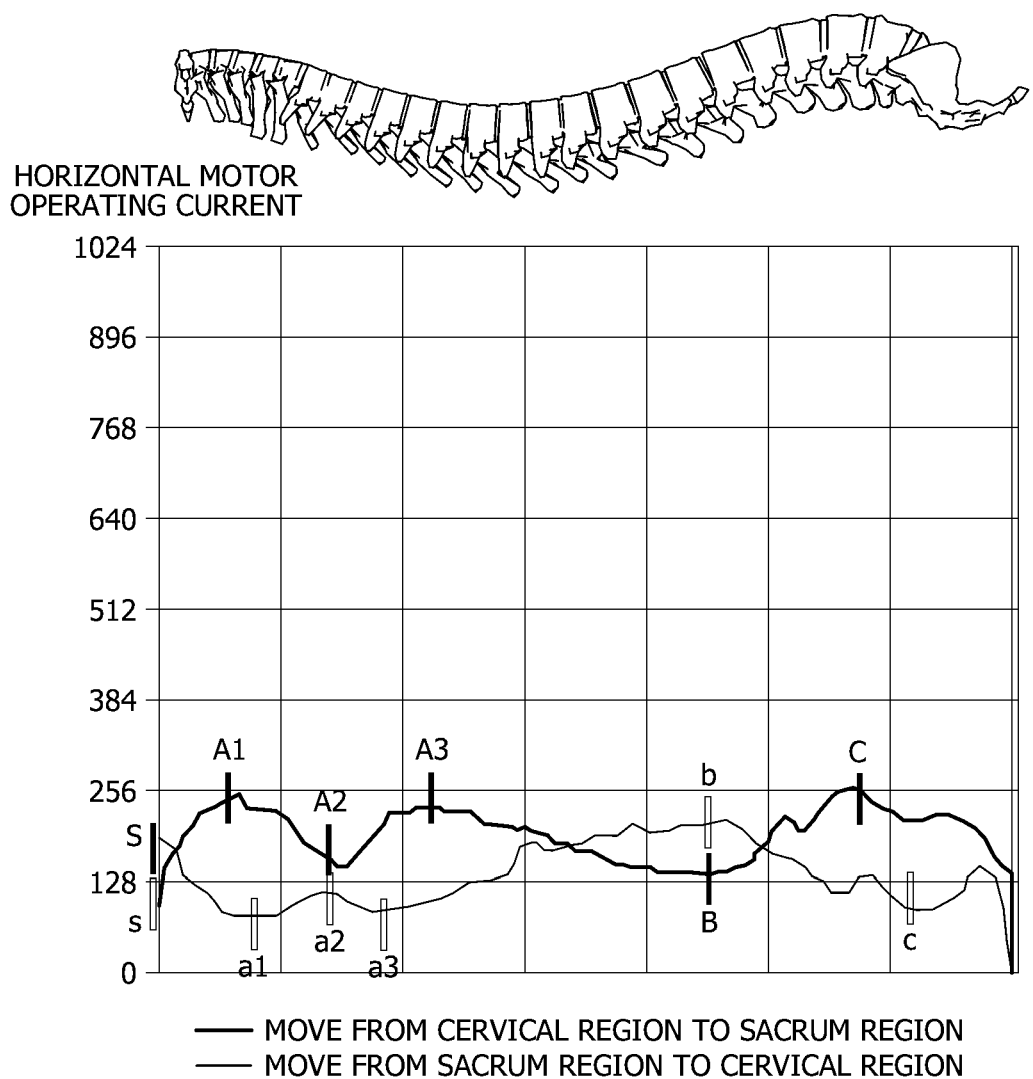
FIG. 8 is a graph showing a human body scan horizontal current data to which a cervical curvature is applied according to the present invention.

The positions of inflection points A1 to C and a1 to c in the data shown in FIG. 8 may be associated with the positions of specific spine bones and it has been proven from tests of 138 subjects that the position of the inflection point C corresponds to the position of a lower side of the spine bone Number 24. In contrast, the positions of spine bones associated with the positions of inflection points A1 to B and a1 to c vary with users, and are not applicable to the method of controlling a human body scan in real-time.

The measurement accuracy of the position of the lower side of the spine bone Number 23 according to the present test is obtained by a calculation of a spine length using a maximum value of a load of a lumbar region, in which the distance from the bottom of the ears (an upper side of the spine Number 1) to the top of the pelvic bone (a lower side of the spine Number 23) is measured, the lower side of the spine Number 24 is detected using the point of the maximum value of a lumbar region in the human scan data (that is, the point 'C' in FIG. 7), and then the spine Number 23 is calculated.

According to the above result, a mean error and a standard deviation of 'B' with respect to 'A' are calculated as shown in FIG. 8, wherein the mean error of measurement of the lower side of the spine Number 23 is 3.63 mm and the standard deviation is 30.85 mm.

According to research on body measurements of Koreans, an average spine length of Koreans is 668 mm, and when the average spine length is divided by 30, the number of spine bones, the average length of one spine bone is calculated as 22.27 mm.

When the degree of accuracy of a human body scan is targeted at the average length of one spine bone, in order to include 70% of all measurement subjects within a target range, a value of "mean error+standard deviation" needs to be 22.27 mm or less in consideration of the specificity of a normal distribution, but the value according to the above measurement result is found to be 34.48 mm, which is outside the target range.

Figure 9:
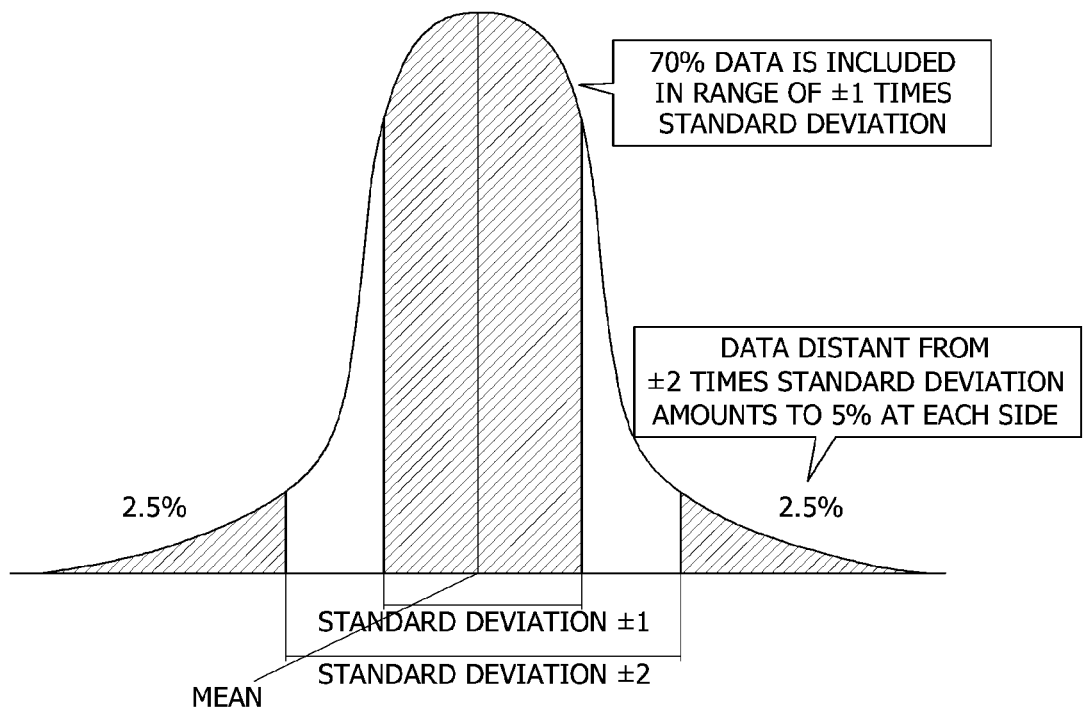
FIG. 9 is a graph showing a specificity evaluation standard of a normal distribution data according to the present invention.

FIG. 9 shows that about 70% of the data is included within a range of ±1 times the standard deviation and about 95% of the data is included within a range of ±2 times the standard deviation according to the specificity of normal distribution data.

Figure 10:
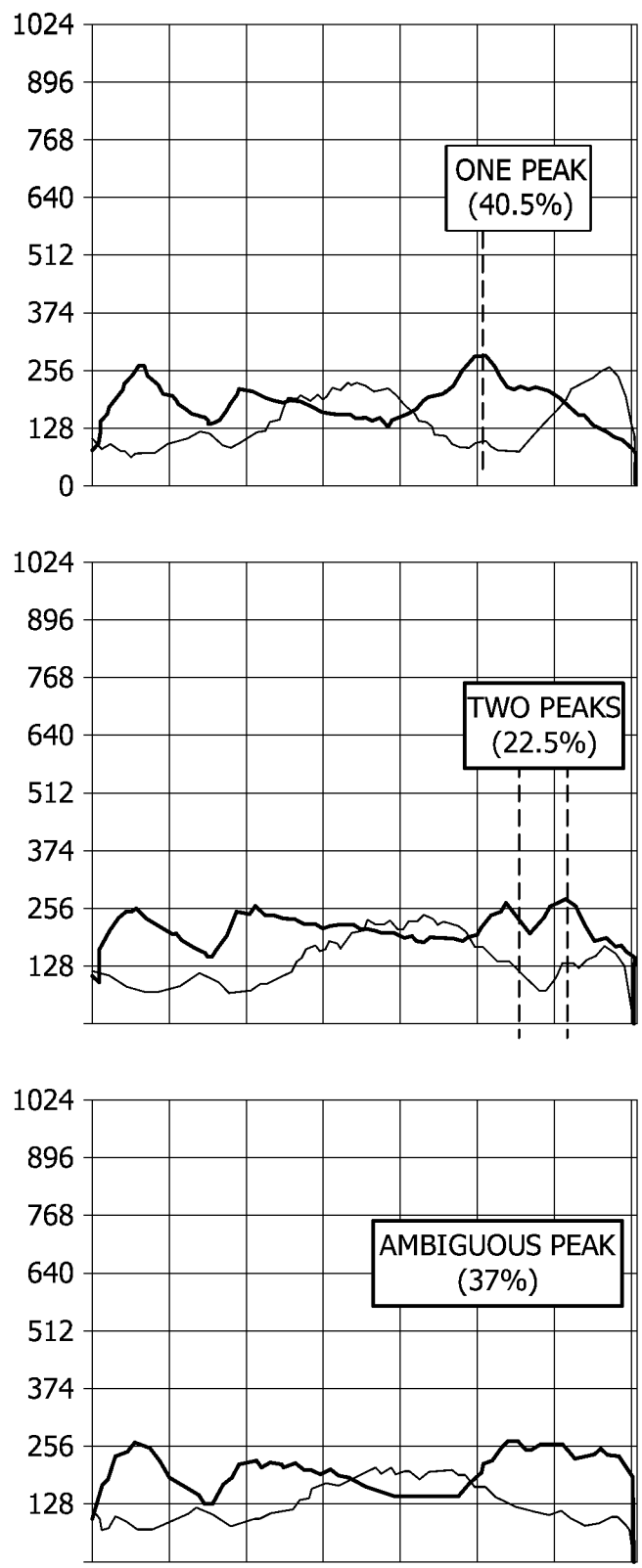
FIG. 10 is a graph showing three types of peak detection of a lumbar region according to a method of controlling a human body scan according to the present invention.

The standard deviation of the measurement result is relatively large in comparison with the mean error because horizontal driving current data of the human body scan is provided into three types as shown in FIG. 10, and unless one peak is clearly detected, a great error occurs in the result of the human body scan.

The main cause of a failure to detect one clear peak is that the acupressure section has two arrays at the upper and lower sides and thus when passing through the pelvic region of the user, has a peak at each of the upper side array and the lower side array or has a peak in the form of the respective peaks summated.

The method of controlling a human body scan in real-time according to the present invention enhances the measurement accuracy with the following improvements.

Figure 11:
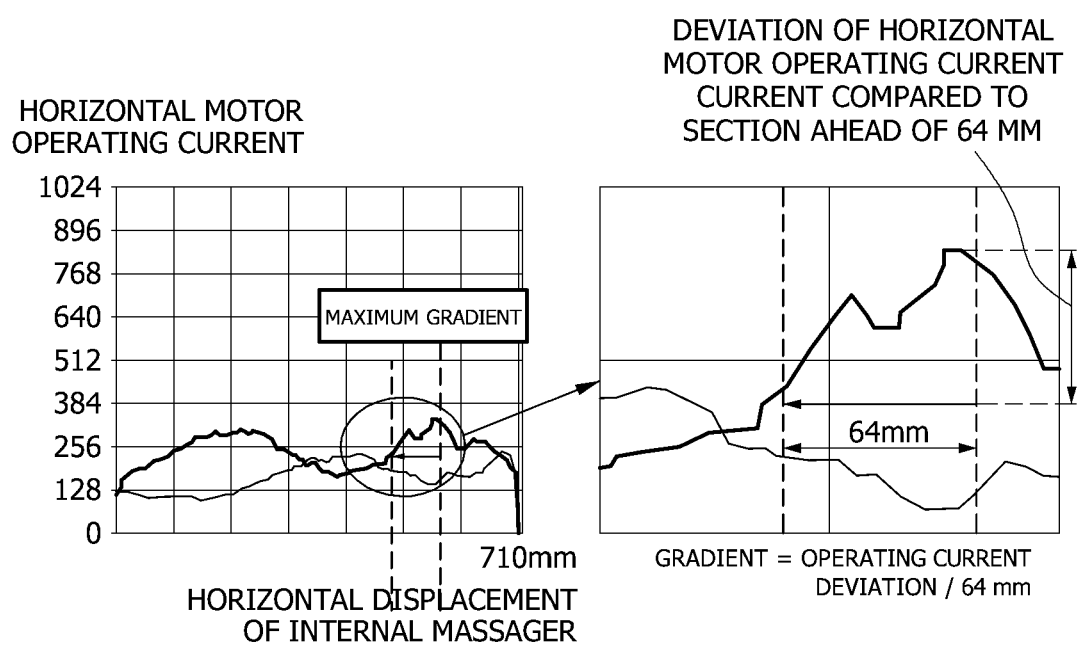
FIG. 11 is a graph showing a detection of a position with a maximum gradient in human body scan horizontal driving current data to which a cervical curvature is not applied according to the present invention.

As shown in FIG. 11, in order to minimize influence from the acupressure section with the two arrays at upper and lower sides, a control method using a point at which human body horizontal driving current data has the maximum amount of variation before and after an interval of 64 mm, which is a top-to-bottom interval of the acupressure section, may be used, and the measurement accuracy of the position of the spine bone Number 23 is as follows.

A test method of calculating a spine length using 12 test subjects and a maximum gradient of the load of the lumbar region is achieved first by measuring the distance from the bottom of the ears (the upper side of the spine Number 1) to the top of the pelvic bone (the lower side of the spine Number 23), and detecting the position of the lower side of the spine Number 24 using the position of the maximum gradient of the lumbar region in the human scan data, and then calculating the spine Number 23.

According to the above result, a mean error and a standard deviation of '13' with respect to 'A' are calculated as in FIG. 8, and the mean error of measurement of the lower side of the spine Number 23 is 6.25 mm and the standard deviation is 15.74 mm.

Since the value of "mean error+standard deviation" is 21.99 mm, which is less than 2.27 mm, the average length of one spine bone, it can be seen that 70% of all measurement subjects are included within the target range.

However, according to the above-described control method, a position tracking is performed only on a specific section, which is an initial stage human body scan of an automatic mode driving, and when the position of an acupoint is changed due to a change of the user's posture after the human body scan, the changed position of the acupoint is not reflected in the heater.

Accordingly, while the above-described method of controlling a human body scan in real-time is only available in a human body scan in a specific section, the following description provides a method of controlling a human body scan in real-time capable of reflecting a changed position in the heater through a constant tracking of an acupoint during a massage process.

In this case, the method is slightly influenced depending on whether the vertical position of the acupressure section is fixed or not.

In addition, different from the conventional method in which the position of an acupoint is calculated after a horizontal full-stroke driving is completely finished and the calculated position of the acupoint is applied to the heater, the following method calculates the position of an acupoint whenever a specific position is passed by through minimal horizontal driving and applies the calculated position to the heater.

In addition, the following method may not only include correcting the position of an acupoint due to the movement of the user during an operation of the heater, but also include, upon a change of the user, determining the change of the user by only a certain section of a horizontal movement and recalculating the position of the acupoint, so the human scan process is included in the massage operation.

Figure 12:
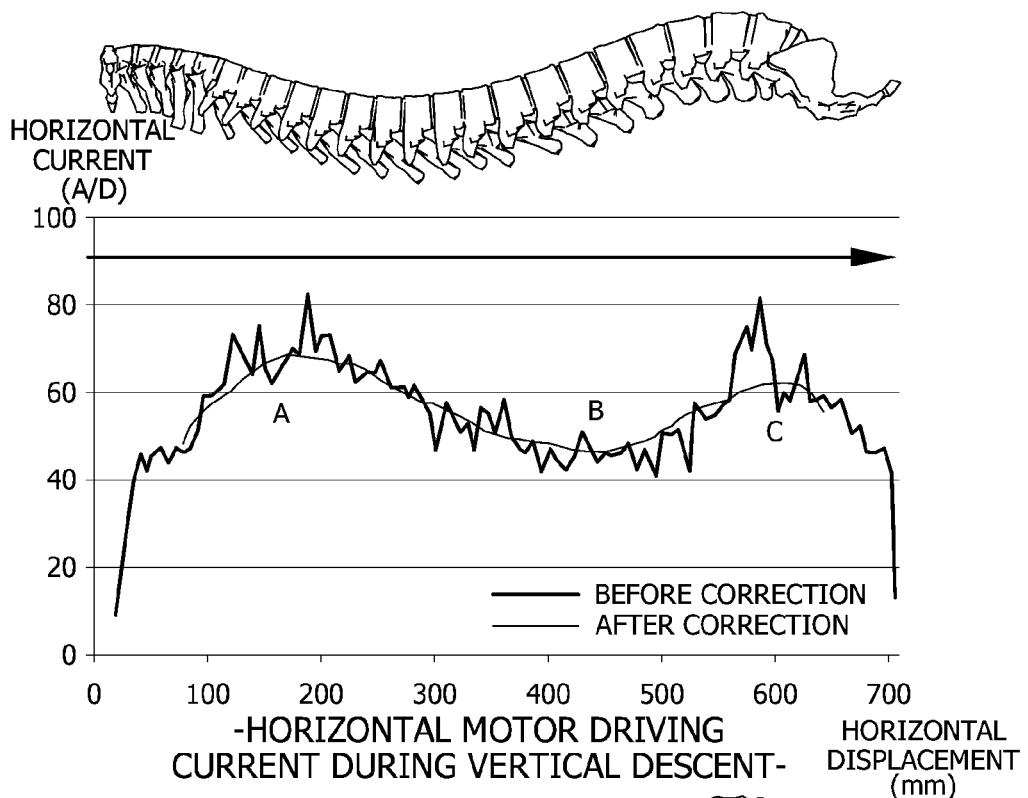
FIG. 12 is a graph showing human body scan horizontal driving current data of a heater according to the present invention.
Figure 12:
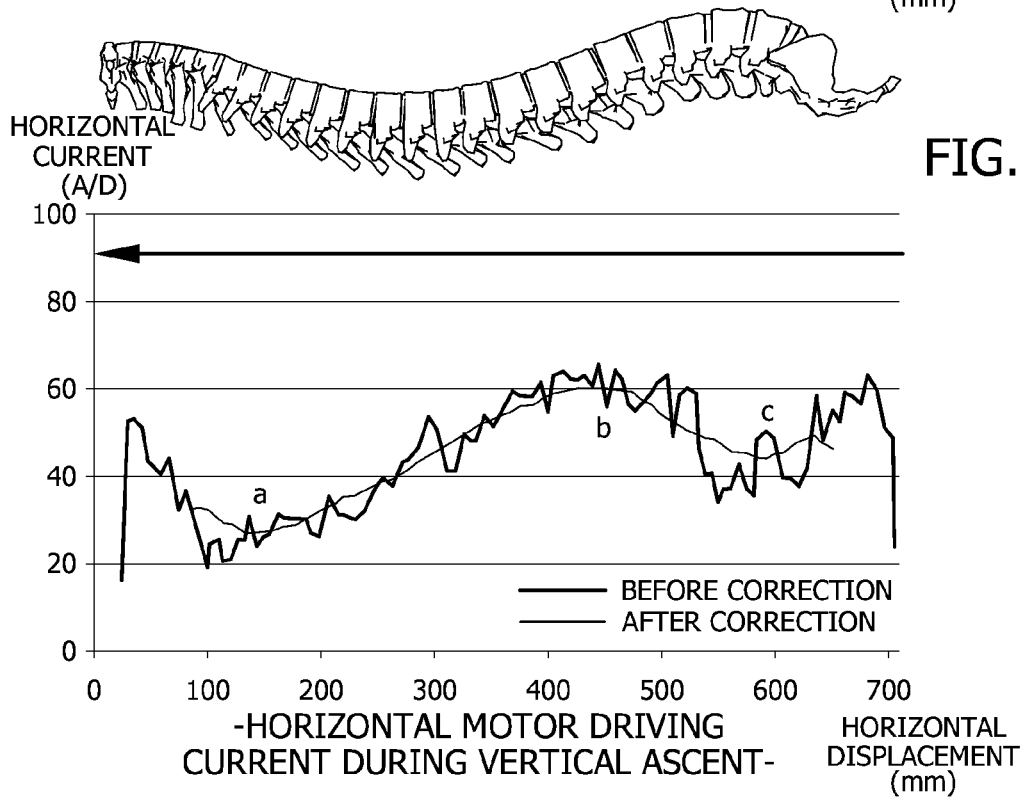

To this end, FIG. 12 shows driving current-measured data of the horizontal driving motor with respect to the horizontal position of the acupressure section when the acupressure section moves from the position of the spine Number 1 of the user to the maximum horizontal stroke section of the heater through horizontal driving in a state in which the acupressure section has the vertical position thereof fixed or operates in an Up/Down state to adjust the acupressure power.

The data has a slight fluctuation in the measured data of the horizontal driving current, but it may be converted into a stable state through a correction using the average for a specific section.

The specific section represents a reference correction range of horizontal displacement, and in order to minimize errors, preferably, the interval between the upper side and the lower side of the acupressure section may be applied to the specific section, and in order to rapidly detect an acupoint, the range of the specific section needs to be properly reduced.

The positions of data inflection points A to C and a to c may be associated with the positions of specific spine bones, and in particularly, it is expected that the position of the inflection point C corresponds to the position of the lower side of the spine bone Number 24 as shown in the existing human body scan control method.

In addition, step (B) of the method of controlling a human body scan in real-time starts from using the positions of A to B and a to c in the detection of acupoints.

In this case, the positions of spine bones associated with the positions of A to B and a to c vary according to users, and are not directly employed as the positions of the spine bones.

However, the distances between A to C and a to c are constant for each user. For example, the position of the inflection point A of the user may be detected at a position shifted by offset X during a massage process, but since the distances from A to B to C and a to c are constant, the positions of B to C and the positions a to c also need to be shifted by the offset in X.

That is, step (C) according to the present invention uses a principle of, when the position of the inflection point A is shifted, not directly tracking the shift of the position of a cervical region bone associated with the position of the inflection point A, but indirectly tracking the shifted positions of other spine bones through the shift of the position of C, which corresponds to the lower side of the spine bone Number 24, according to the shift of the inflection point A.

In the above-described tracking principle, it is important to distinguish the positions of A to C and a to c with respect to inflection points of the horizontal motor driving current.

Referring to the data in FIG. 12, it is observed that A, C, a, and c are characterized in increasing and then decreasing, and B and b are characterized in decreasing and then increasing.

However, these characteristics may appear even at other points temporarily, not only at the positions of A to C and a to c, and thus the other points may be erroneously determined to be the positions of A to C and a to c.

In addition, A and C have the same characteristics as each other and a and c have the same characteristics as each other, and thus the distinguishment between A and C and between a and c is ambiguous.

Accordingly, when determining the positions of A to C and a to c, a process of identifying the inflection points by dividing the entire horizontal moving section into three regions is used.

When dividing the horizontal movement section into three regions, the length of the spine according to the user's height needs to be identified.

In the case of a heater having a horizontal movement range of 710 mm according to the present invention, it is known that a stable human body scan is performable on a user with a height of 1200 mm to 1864 mm because the height corresponds to the length of the spine of 498 mm to 774 mm on the basis of the average ratio of the spine length to the height of 41.53% according to research on body measurements of Koreans.

The value of 774 mm is a value of 710 mm, which is the horizontal movement section, plus 64 mm, which is the top-to-bottom distance of the acupressure section.

A user having a westernized body type is characterized in that the length of the upper body is shorter than the length of the lower body in comparison with Koreans. In this case, the maximum height which ensures a stable human body scan may be larger than 1864 mm.

The reason for noting the user's height is that when the horizontal movement section is divided into three regions, the positions of A to C and a to c need to be detected without any exception for the length of the spine from 498 mm to 774 mm.

To this end, the positions of A, B, C, a, b, and c are measured on five test subjects through a human body scan test, and the results are shown in Table 1 below.

Also, using the test results, points for dividing regions may be set such that points A and a are positioned in the first region, points B and b are positioned in the second region, and points C and c are positioned in the third region. The points are shown in FIG. 13.

TABLE 1

|   | Vertical height | A | B | C | a | b | c |
|---|---|---|---|---|---|---|---|
| 1 | MIN | 178 | 430 | 606 | 60 | 385 | 565 |
|   | MAX | 163 | 413 | 647 | 123 | 421 | 650 |
| 2 | MIN | 101 | 281 | 520 | 72 | 291 | 487 |
|   | MAX | 95 | 325 | 523 | 101 | 317 | 545 |
| 3 | MIN | 214 | 423 | 572 | 72 | 391 | 542 |
|   | MAX | 225 | 418 | 589 | 72 | 364 | 537 |
| 4 | MIN | 198 | 407 | 575 | 64 | 349 | 542 |
|   | MAX | 231 | 421 | 609 | 91 | 393 | 565 |
| 5 | MIN | 167 | 358 | 556 | 72 | 331 | 509 |
|   | MAX | 160 | 388 | 586 | 112 | 331 | 548 |
| Total | Horizontal min | 96 | 281 | 520 | 60 | 291 | 487 |
|   | Horizontal max | 231 | 430 | 647 | 123 | 421 | 650 |

Figure 13:
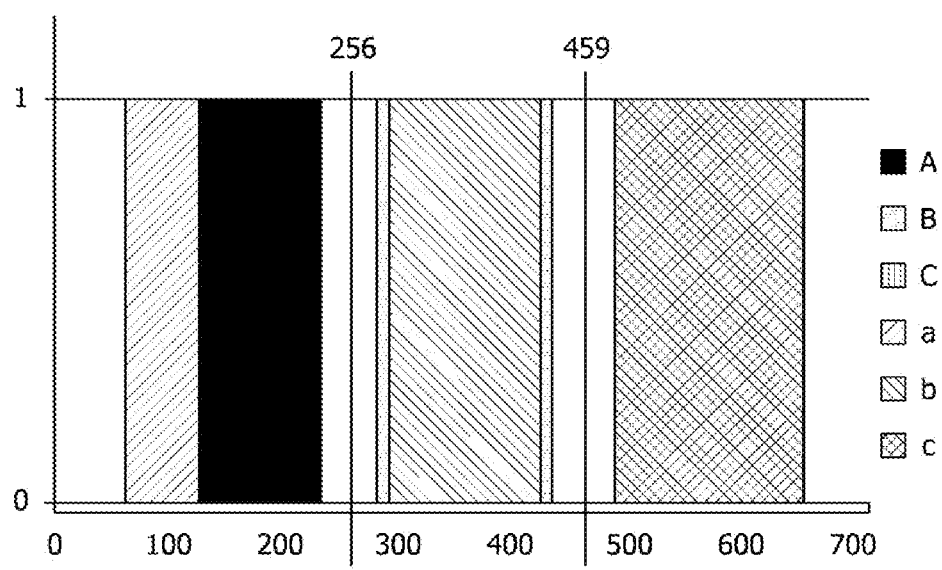
FIG. 13 is an illustration derived from using the test results showing points for dividing regions may be set such that points A and a are positioned in the first region, points B and b are positioned in the second region, and points C and c are positioned in the third region.

According to the above results, it can be seen in FIG. 13 that the detection regions of A to C and a to c do not overlap each other when the horizontal movement section is divided at points at distances of 256 mm and 459 mm from a scan start position.

In addition, with regard to the above data, in the measurement of the positions of A to C and a to c, the maximum and minimum values of the average of a specific section (±64 mm) of the driving current of the horizontal driving motor are used.

When the maximum gradient is used as shown in FIG. 11 instead, more accurate data extraction is possible.

During a subsequent massage operation, a method of detecting the positions of A to C and a to c based on the above description is performed as follows.

For the horizontal driving current at the time of the horizontal descent, the maximum value in the first region is A, the minimum value in the second region is B, and the maximum value in the third region is C.

For the horizontal driving current at the time of the horizontal ascent, the minimum value in the first region is a, the maximum value in the second region is b, and the minimum value in the third region is c.

When the positions of A to C and a to c are changed according to movement of the user, the positions of the boundaries for dividing the three regions need to be changed as well.

In this regard, there is another aspect to be further considered. That is, a determination method when the interval between acupoints is changed due to the change of the user during use of the heater, that is, upon a change in the ratio of each of the lengths between A and C, B and C, a and C, b and C, and between c and C, relative to the length between the scan start position and C.

In other words, a primary concept of applying the offset corresponding to a changed value to the positions of all acupoints in response to a change of a single position of A to C and a to c is combined with a secondary concept of performing a correction on all acupoints through a section ratio by a ratio change due to a change of multiple positions of A to C and a to c, thereby compensating for the method of controlling a human body scan in real-time.

To this end, the method of controlling a human body scan in real-time according to the present invention may further include a process of correcting the positions of the acupoints through the section ratio using the data shown in Table 1 above.

When the vertical height of the acupressure section is the lowest, test subject 1 has the position of A at 178 mm and the position of B at 430 mm.

When the position of A is shifted to a point of 200 mm during the massage operation, the position of B is provided as 430+(200−178)=452 mm by applying the above-described primary concept.

When the movement of the user is natural movement according to an operation of the product, and B is passed after A is passed without any special operation (without a conversion in the horizontal direction, stop, or a 3D motion in the middle of the operation), the position of B has to be detected at 452 mm as calculated above.

When the position of B is detected at a position different from 452 mm, it is determined that the user is not simply moved but is changed. In this case, instead of the offset shift for the acupoint through the primary concept, a correction using a section ratio for acupoints through the secondary concept is needed.

Also, a predetermined amount of measurement error range needs to be applied to 452 mm, and the secondary concept is applicable only when two positions are consecutively passed with respect to the positions A to C and a to c.

Assuming that the position of B is detected at 440 mm rather than 452 mm and a measurement tolerance of 10 mm is applied, the position error of B exceeds the measurement tolerance of 10 mm, and thus B is subject to application of the secondary concept.

In this case, it can be seen that the interval between A and B is reduced from 430−178=252 mm to 440−200=240 mm. As a result, when the distance from a current acupoint to another acupoint in the previous step is R and the distance from a current acupoint to another acupoint in the current step is Rn, Rn is expressed as follows.

'$Rn = R \times$(current distance between two points/previous distance between two points)=$R \times 240/252$' [Equation 1]

A changed position Pn of a specific acupoint at a distance from the scan start position is as follows.

'$Pn$=current position−$Rn$' [Equation 2]

When the position of the specific acupoint is located at a distance P from the scan start position, a variation of position Dp of the changed specific acupoint Pn is as follows.

'$Dp = P - Pn$' [Equation 3]

According to an operation concept of the heater, a value of Dp which is higher than or equal to a predetermined value may be determined as the change of the user, and a new process, such as a remote controller display and a driving mode restart, may be applied.

The specific horizontal positions are distinguished by a driving current inflection point of the horizontal driving motor as described above, and in a state in which a normal target acupressure power is set, the vertical height at a specific horizontal position is provided to be similar to a specific value of the standard spinal curvature.

When the vertical height is lower than the specific value, it means that the target acupressure power is set to be low, and when the vertical height is higher than the specific value, it means that the target acupressure power is set to be high.

In addition, since the deviation between a current set acupressure power and the proper target acupressure power is proportional to the deviation between a current vertical height and a vertical height at the specific position, a correction value for a current target acupressure power may be calculated using the proportional relation in order to calculate the proper target acupressure power.

In addition, vertical height references of the acupressure section at specific horizontal positions implemented through the method of controlling acupressure power in real-time when the target acupressure power is properly set may be employed as follows.

'A: vertical maximum height, B: ¼ position of vertical maximum height, C: ¾ position of vertical maximum height'

'a: vertical maximum height, b: ¾ position of vertical maximum height, c: vertical minimum height'

In this case, a method of automatically calculating the target acupressure power starts with the target pressure at the lowest value.

When the operation of the heater starts, the target acupressure power is the lowest value, and thus the acupressure section ascends to the maximum vertical height regardless of the current acupressure power.

Accordingly, the operation of the heater starts from the cervical region in which the vertical height ascends to the maximum level regardless of the body type.

During the operation with the target acupressure power at the lowest value, the vertical position of the acupressure section is always the maximum vertical height, so that the target acupressure power gradually increases through the vertical height comparison at each specific position.

Upon completion of the calculation of the target acupressure power via the vertical height comparison with respect to six specific horizontal positions through the horizontal descending and ascending of the acupressure section, the target acupressure power is applicable to the massage strength. When the change of the user is determined during the operation of the product, the above-described target acupressure power automatic control method needs to be newly applied.

In addition, with regard to the positions A, a, and c, of which the vertical height reference is the highest or the lowest, there may be a case in which the vertical height comparison is not performable. Accordingly, it is preferable to reflect a deviation between the measured acupressure power and the target acupressure power in calculating a new target acupressure power, and in order to apply a proper ratio for the deviation, a correction constant 'F' may be used.

In addition, a method of target acupressure power automatic calculation may directly convert the target acupressure power through the vertical position comparison at each specific horizontal position, but in order to prevent a sudden change in the target acupressure power and prevent a calculation error of the total target acupressure power due to an instantaneous measurement error, a correction constant 'P' may be applied such that a stepwise correction is performed. The correction constant 'P' may be set to 0.5, and may be properly changed according to a use condition.

Finally, a final target acupressure power is calculated by applying the average value for the correction values at six specific positions.

In this case, a new target acupressure power and the final acupressure power using the correction constants F and P are calculated by the following expressions.

New target acupressure power=previous target acupressure power+correction factor $F$×(measured acupressure power−target acupressure power)+correction constant $P$×(vertical reference position−vertical current position) [Equation 4]

Final target acupressure power=(summation of target acupressure powers at positions of $A$ to $C$ and $a$ to $c$)/number of specific positions [Equation 5]

As described above, since the measurement and control is achieved in real-time when the vertical height of the acupressure section is controlled according to weight-measured data of the load cell, part and all sections are individually or collectively controlled with a desired target acupressure power regardless of movement of the user.

Although the method of controlling a human body scan in real-time according to the present invention has been described with reference to the accompanying drawings, in relation to a specific form and direction, it should be appreciated by those skilled in the art that various modifications and changes are possible without departing from the scope and sprit of the present invention.

What is claimed is:

1. A method of controlling acupressure power in real-time, the method comprising the steps of:
   (a) setting a reference vertical height and a range of acupressure power to reference vertical height for each horizontal position of an acupressure section and setting a target acupressure power within a range of the reference vertical height, and determining a specific horizontal position corresponding to an inflection point of a measured value of a driving current applied to a horizontal driving motor during forward and backward movement of the acupressure section (S100);
   (b) calculating a current measured acupressure power from measured data of a load of a user applied to a load cell and calculating a new target acupressure power in a massage process by reflecting a deviation between a vertical height of the acupressure section at the specific horizontal position and the reference vertical height at the specific horizontal position stored in a database (S200); and
   (c) comparing the target acupressure power with the current measured acupressure power and controlling a vertical height of the acupressure section (S300).

2. The method of claim 1, wherein, in step (c) of operation S300:
   the acupressure section vertically descends or vertically ascends when the current measured acupressure power is higher than the target acupressure power or the current measured acupressure power is lower than the target acupressure power; and
   the acupressure section stops vertical driving when the current measured acupressure power is equal to the target acupressure power.

3. The method of claim 2, wherein, when a current vertical height of the acupressure section is outside the range of the reference vertical height, the measured acupressure power is assigned a predetermined margin value.

4. The method of claim 1, wherein step (a) of operation S100 further comprises (a') adopting the target acupressure power with a minimum value.

5. The method of claim 4, wherein the inflection point of the driving current-measured value is calculated as a specific spine position of a current user, and when a current spine position corresponding to the driving current-measured value applied to the horizontal driving motor during a horizontal movement of the acupressure section in a massage process is different from the specific spine position, a position of an acupoint is corrected with an offset by a deviation between the current spine position and the specific spine position.

6. The method of claim 5, wherein, when a distance ratio for acupoints of previous spine positions is changed to a distance ratio for acupoints of current spine positions due to a change of the user, a ratio for the acupoints is corrected.

7. A method of controlling a human body scan in real-time, the method comprising the steps of:
   (A) collecting electric current variation value data according to a driving of a horizontal motor, setting a variation section of a current, and extracting position information at acupoints corresponding to a maximum inflection point and a minimum inflection point of the variation section;
   (B) when a position of an acupoint of a current user during a massage process is different from the position of the acupoint corresponding to step (A), determining whether it is a movement of the user or a change of the user that caused a difference between the positions and calculating a correction value according to the difference between the positions; and
   (C) correcting the positions of the respective acupoints of the current user by the correction value calculated in step (B).

8. The method of claim 7, wherein, when a distance between acupoints of the current user during the massage process is different from a distance between previous acupoints extracted in step (A), a distance ratio for the acupoints of the current user is corrected by a ratio of the distance between the current acupoints and the distance between the previous acupoints.

* * * * *